(12) United States Patent
Yamazaki et al.

(10) Patent No.: US 7,344,512 B2
(45) Date of Patent: Mar. 18, 2008

(54) PROTECTOR AND BLOOD PUMP SYSTEM

(75) Inventors: Kenji Yamazaki, Tokyo (JP); Nobuaki Aizawa, Nagano (JP)

(73) Assignee: Sun Medical Technology Research Corporation, Nagano (JP)

( * ) Notice: Subject to any disclaimer, the term of this patent is extended or adjusted under 35 U.S.C. 154(b) by 737 days.

(21) Appl. No.: 10/387,053

(22) Filed: Mar. 12, 2003

(65) Prior Publication Data

US 2003/0176835 A1 Sep. 18, 2003

(30) Foreign Application Priority Data

Mar. 15, 2002 (JP) ............... 2002-072075

(51) Int. Cl.
*A61M 37/00* (2006.01)

(52) U.S. Cl. ............ 604/6.11; 604/263; 604/264; 604/268; 604/273; 604/304; 604/305; 604/307; 604/308; 602/52; 602/46; 602/41; 602/37

(58) Field of Classification Search ......... 604/6.11, 604/263, 264, 268, 273, 304, 305, 307–308; 602/3, 21, 36, 37, 41–46, 52

See application file for complete search history.

(56) References Cited

U.S. PATENT DOCUMENTS

| 4,265,233 | A | * | 5/1981 | Sugitachi et al. ........... 604/304 |
| 4,645,492 | A | * | 2/1987 | Weeks .................... 604/174 |
| 4,648,391 | A | | 3/1987 | Ellis |
| 5,112,313 | A | * | 5/1992 | Sallee ..................... 604/180 |
| 5,116,324 | A | * | 5/1992 | Brierley et al. ............. 604/180 |
| 5,593,395 | A | * | 1/1997 | Martz .................... 604/304 |
| 5,685,859 | A | * | 11/1997 | Kornerup ................. 604/180 |
| 5,758,660 | A | | 6/1998 | Lokken |
| 6,124,521 | A | * | 9/2000 | Roberts .................... 602/54 |
| 6,827,707 | B2 | * | 12/2004 | Wright et al. ............. 604/180 |

FOREIGN PATENT DOCUMENTS

| DE | 10 028 512 | 2/2002 |
| EP | 0 082 596 | 11/1982 |
| JP | 2000-140125 | 5/2000 |

\* cited by examiner

*Primary Examiner*—Tatyana Zalukaeva
*Assistant Examiner*—Ginger Chapman
(74) *Attorney, Agent, or Firm*—Hogan & Hartson LLP

(57) ABSTRACT

A protector effectively suppresses infections. The protector protects a tube entry part, where a tube passes through the skin of a living body, from infections, and includes a sticking part that is stuck onto the skin of the living body in a periphery of the tube entry part, and a covering that covers the tube entry part, forms an internal space that surrounds the tube entry part, and has a passage through which the tube passes. The covering is provided with an opening that can be freely opened and closed with a cap or the like.

13 Claims, 15 Drawing Sheets

400

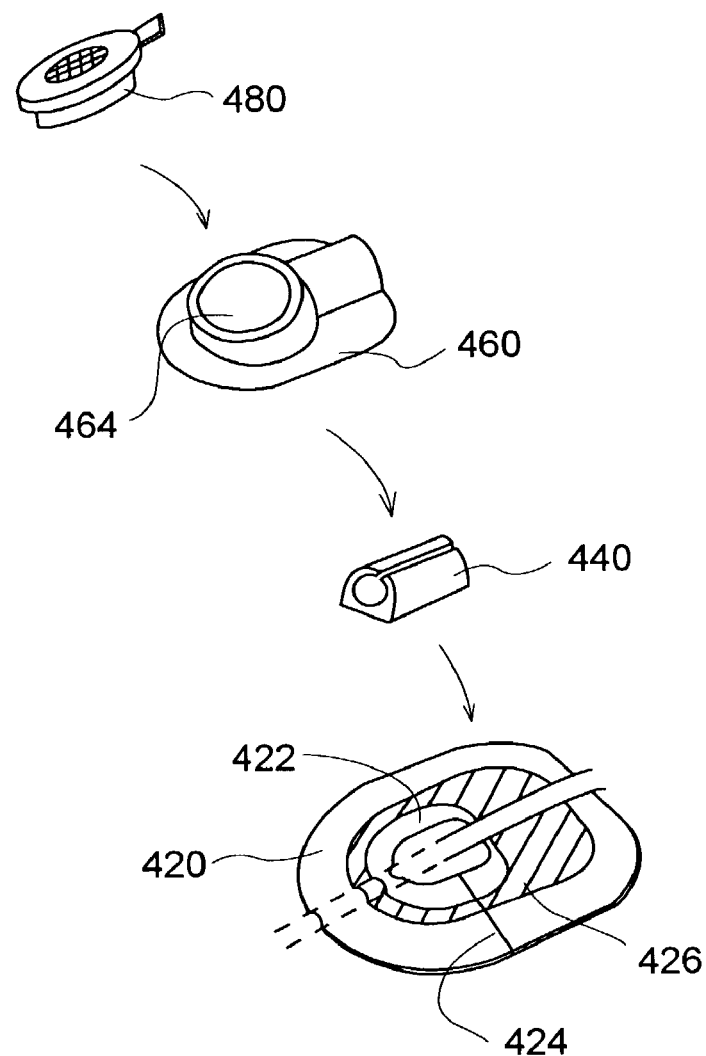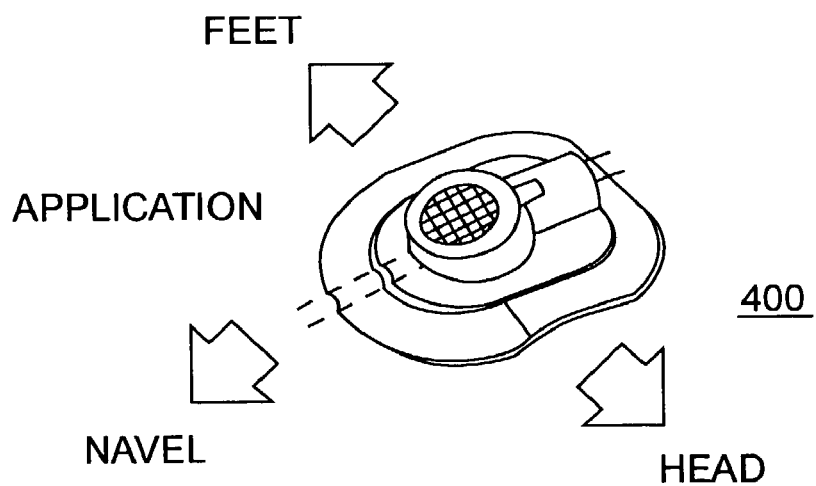
FIG. 13

BODY

DISINFECTANT

421

PROTECTOR AND BLOOD PUMP SYSTEM

BACKGROUND OF THE INVENTION

1. Field of the Invention

The present invention relates to a protector that protects a part of a living body where medical equipment, such as tubes and cables that are implanted in the body, enters the body from infection (note that such medical equipment is collectively referred to as "tubes" hereinafter). The invention also relates to the components used in such a protector and to a blood pump system that uses such a protector.

2. Related Art

A variety of medical treatments have been conventionally performed using medical equipment, such as tubes, that is implanted in a living body. Examples of such treatments include the use of artificial hearts during and following heart surgery, dialysis, and Continuous Ambulatory Peritoneal Dialysis (hereinafter, "CAPD"). Infections at a part where a tube passes through the skin (hereinafter "tube entry part") pose a significant clinical problem during such treatments. At the tube entry part, the bonding forces between the body tissue near the skin and the surface of the tube are weak, so that external forces can easily detach the surface of the tube from the body tissue. Bacteria can enter the skin tissue at such parts, thereby causing infections. Once the tube entry part has become infected, the infection progresses along the tubes deep into the body tissue, which increases the risk of serious complications such as septicemia.

In order to solve the above problem, the present applicant has developed a fixing assembly and has disclosed this assembly in Japanese Laid-Open Patent Application No. 2000-140125. FIG. 16 is a cross-sectional drawing of this fixing assembly. As shown in FIG. 16, the fixing assembly 910 protects the tube entry part where a tube 990 passes through the skin of a living body from infection, and includes a sticking part 920, which is stuck onto the skin 902 of the living body in a periphery of the tube entry part, and a covering 940 which covers the tube entry part, forms an internal space 908 that surrounds the tube entry part, and includes a passage 980 through which the tube 990 passes.

The fixing assembly 910 makes it difficult for a tube that passes through the skin of a living body to move, so that external forces are prevented from detaching the tube from the body tissue, which is effective in suppressing infections. Additionally, when this fixing assembly 910 is used, the internal space 908 that surrounds the tube entry part can be filled with medication, so that infections can be suppressed even more effectively.

However, when there is an infection at the tube entry part, there is a very high risk of the infected area progressing along the tube and spreading deep into the body tissue to cause serious complications such as septicemia, so that it is necessary to provide even greater protection against infections.

SUMMARY OF THE INVENTION

It is an object of the present invention to provide a protector that can suppress infections even more effectively. It is a further object of the present invention to provide components used in such a protector and a blood pump system that uses this protector.

A protector of the present invention protects a part (hereinafter "tube entry part") where a tube, cable, and the like (hereinafter "tube") passes through the skin of a living body from infection and includes a sticking part that is stuck onto the skin of the living body in a periphery of the tube entry part, and a covering that covers the tube entry part, forms an internal space that surrounds the tube entry part, and has a passage through which the tube passes, wherein the covering is provided with an opening that can be freely opened and closed.

With the protector of the present invention, a passage for a tube is provided in the covering, so that it becomes difficult for a tube, etc., that passes through the skin of a living body to move. This means that external forces can be effectively prevented from detaching the tube from the body tissue. Also with the protector of the present invention, the internal space that surrounds the tube entry part can be filled with medication, which is even more effective in preventing infections.

In addition, with the protector of the present invention, the covering is provided with an opening that can be freely opened and closed. Via this opening, it is easy to administer medication to the tube entry part and to treat the tube entry part as necessary, which means that infections can be prevented even more effectively. Also, via this opening, air can pass through to the tube entry part so as to dry the tube entry part. This suppresses the propagation of germs and makes it possible to prevent infections even more effectively.

With the above construction, since the tube pass through the skin or percutaneous of a living body, the tube entry part can be expressed as "a percutaneous part."

It is preferable for the above protector to further include a cap that closes the opening.

With the above construction, the cap can be normally closed. This prevents bacteria in the air from reaching the tube entry part, so that infections can be prevented even more effectively.

It is also preferable for the cap of the above protector to be breathable and to function as a filter that prevents bacteria from entering.

With the above construction, moisture and bacteria can be prevented from entering by closing the cap. In addition, in this closed state air can pass through to the tube entry part so as to dry the tube entry part. This suppresses the propagation of germs and makes it possible to prevent infections even more effectively.

It is also preferable for the cap of the above protector to include an outer frame, which is made of a resinous material, and a film, which is disposed inside the outer frame and is breathable, the outer frame and the film being integrated. The outer frame and the film are integrated by adhesion, welding, insert molding or the like.

With the above construction, the outer frame is made of a resinous material, so that the shocks experienced when the cap is opened and closed are dampened, which effectively prevents external forces from detaching the tube from the body tissue. This also reduces the pain experienced by the patient when the cap is opened and closed. In addition, when the outer frame and breathable film are integrated, the construction of the cap is highly reliable, which means that infections can be prevented even more effectively. In view of ease of use and adhesion, it is preferable for the outer frame to have a Shore hardness of around 50 A.

With the above protector, it is also preferable for the film to be composed of a polyurethane film in which silk protein powder (or silk protein grains) has/have been dispersed. This construction is suited to preventing moisture, bacteria, etc., from passing through the film while ensuring that the film is breathable.

For the above protector, as one alternative, a film produced by laminating a polyurethane film, in which silk protein powder has been dispersed, and a nylon tricot film can be favorably used as the film. Such a film has superior breathability, so that the tube entry part can dry quickly, thereby effectively suppressing infections. The film also provides superior waterproofing, which protects the tube entry part from moisture, thereby suppressing infections more effectively. The film also has superior strength, which makes the cap easy to handle and easy to maintain. Since the film has an antibacterial action, bacteria can be prevented from reaching the tube entry part, which also suppresses infections. As the film is transparent, the condition inside the protector can be observed without opening the cap. This reduces the number of times the cap is opened and closed, which also suppresses infections.

As another alternative, a thermoplastic polyester film may be favorably used as the film. Such a film has superior breathability, so that the tube entry part can dry quickly, thereby suppressing infections. As the film is also very transparent, the condition inside the protector can be observed easily without opening the cap. This reduces the number of times the cap is opened and closed, which also effectively suppresses infections. The film has superior strength, which makes the cap easy to handle and easy to maintain. In addition, since the film is waterproof, the tube entry part is protected from moisture, thereby suppressing infections.

As other alternatives, a film produced by laminating a nylon film and a polytetrafluoroethylene porous film or a film produced by laminating a polytetrafluoroethylene porous film and a moisture-permeable non-porous film may be favorably used as the film. Such films provide superior waterproofing, so that the tube entry part can be protected from moisture, thereby effectively suppressing infections. Since the films also have a superior antibacterial action, bacteria are prevented from reaching the tube entry part, which further suppresses infections. The films also have superior strength, which makes the cap easy to handle and easy to maintain. Since the films are breathable, the tube entry part can be dried, which also suppresses infections.

Antibacterial paper can also be favorably used as the film. Antibacterial paper has superior breathability, so that the tube entry part can be dried quickly, thereby effectively suppressing infections. Since the paper also has a superior antibacterial action, bacteria are prevented from reaching the tube entry part, which further suppresses infections. Such paper also has a superior strength, which makes the cap easy to handle and easy to maintain.

As yet another alternative, a nonwoven polypropylene material may be favorably used as the film. Such nonwoven material has superior breathability, so that the tube entry part can be dried quickly, which is effective in suppressing infections. Since such material also provides superior waterproofing, the tube entry part is protected from moisture, which further suppresses infections. The material also has an antibacterial action, so that bacteria are prevented from reaching the tube entry part, which further suppresses infections. As such material is also strong, the cap is easy to handle and easy to maintain.

As yet another alternative, polyurethane film may be favorably used as the film. Such film has superior breathability, so that the tube entry part can be dried quickly, thereby effectively suppressing infections. Since the film also provides superior waterproofing, the tube entry part is protected from moisture, which further suppresses infections. The material also has a superior antibacterial action, so that bacteria are prevented from reaching the tube entry part, which suppresses infections even more effectively. As the film is also very transparent, the condition inside the protector can be observed easily without opening the cap. This reduces the number of times the cap is opened and closed, which is also effective in suppressing infections.

As yet another alternative, a film produced by laminating a polyethylene film on a polytetraflouroethylene porous film may be favorably used as the film. Such film has superior breathability, so that the tube entry part can be dried quickly, thereby effectively suppressing infections. Since the film also provides superior waterproofing, the tube entry part is protected from moisture, which further suppresses infections. The material also has a superior antibacterial action, so that bacteria are prevented from reaching the tube entry part, which suppresses infections even more effectively. In addition, the film is strong, which makes the cap easy to handle and easy to maintain.

As yet another alternative, a film produced by laminating a nonwoven material on a microporous multilayer polyolefin film may be favorably used as the film. Such film has superior breathability, so that the tube entry part can be dried quickly, thereby effectively suppressing infections. Since the film also provides superior waterproofing, the tube entry part is protected from moisture, which suppresses infections even more effectively. In addition, the film has superior strength, which makes the cap easy to handle and easy to maintain.

The outer frame is preferably made of a polyester elastomer. By doing so, the outer frame and the film can be integrally formed by adhesion, welding, insert molding or the like.

It is preferable for the above protector to further include a tube fixing part that fixes the tube to the protector.

With the above construction, movement of the tube that passes through the skin of the living body is effectively suppressed, which effectively prevents the tube from becoming detached from the body tissue due to an external shock.

With the above construction, the tube fixing part can be separated from the sticking part or the covering and can be integrated with the sticking part or the covering.

It is also preferable for the tube fixing part to be constructed so that the tube fixing part (i) is capable of being fixed to one of the sticking part and the covering and (ii) has a hole whose inner surface corresponds to an outer surface of the tube, a cut being provided in the tube fixing part in the axial direction.

With the above construction, the tube is fixed to the protector via the tube fixing part so that movement of the tube that passes through the skin of the living body can be reliably suppressed. In addition, since the inner surface of the tube fixing part corresponds to the outer surface of the tube, movement of the tube is reliably suppressed and it becomes extremely difficult for bacteria to reach the inner space that surrounds the tube entry part. Since a cut is provided in the axial direction in the tube fixing part, it is easy to place the tube into the hole.

The tube fixing part should preferably have a Shore hardness of around 40 A. In other words the tube fixing part should preferably have a hardness of around 40 -A on a Shore durometer scale. This makes it possible for the cut to be opened using the fingers, which facilitates operations that fix and remove the tube to and from the protector. Silicone rubber may be used preferably as the material for the tube fixing part. The tube fixing part may be fixed to the sticking part from the beginning.

It is also preferable for the covering in the above protector to have a Shore hardness in a range of 30 A to 90 A. In other words it is also preferable for the covering in the above protector to have a hardness in a range of 30 -A to 90 -A on a Shore durometer scale.

When the Shore hardness is 90 A or below, it is difficult to apply stress to the sticking part, which makes it difficult for the covering to become detached from the sticking part. Also, since the sticking part is flexible so as to bend in accordance with the shape of the body, pressure sores and the like can be avoided. Also, if the Shore hardness is 30 A or above, a certain degree of rigidity is achieved, so that the shape of the internal space for protecting the tube entry part can be maintained. When the hardness is in the stated range, it is easy to attach a cap to the covering. In view of this, it is more preferable for the covering to have a Shore hardness in a range of 35 A to 80 A. It is preferable for the covering to be made of resin, with silicone rubber being even more preferable.

It is preferable for the sticking part of the above protector to have a multilayer construction including a foam layer and an adhesive layer or singlelayer construction including an adhesive layer.

With the above construction, since the entire sticking part is flexible and is fixed onto the skin through adhesion, the sticking part can easily bend in accordance with the shape of the skin at that part of the body, which makes it easy to attach the sticking part to the skin. It also becomes difficult for pressure sores and the like to develop. Since the sticking part is light, the burden placed upon the patient can be reduced.

It is preferable for the foam layer in the above protector to be formed of polyisobutylene foam. Polyisobutylene foam is compatible with medications such as ointments, so that a wide variety of medications may be selected.

It is also preferable for the adhesive layer in the above protector to be formed of a skin protective agent. If a skin protective agent is used, the effect of the protector on the skin is reduced, so that the protector can be used for a long time. Also, patient discomfort due to rashes can be reduced, and reductions in adhesion to the skin due to the development of a rash can be suppressed. A karaya gum-type skin protective agent, a CMC-type skin protective agent, or a mixed skin protective agent including the karaya gum and CMC types may be used as the skin protective agent, with a mixed skin protective agent that is made mostly from karaya gum and citrus pectin being especially preferable. Before the sticking part is used, detachable backing paper may be placed on the surface of the adhesive layer to protect the sticky surface.

It is preferable for the sticking part to be around 3.3 mm thick. In multilayer case, the foam layer is around 1.4 mm thick and the adhesive layer is around 1.9 mm thick. The thickness of the sticking part may be set in accordance with the size, etc., of the sticking part. To make the protector easy to use, the opening in the sticking part should preferably have a diameter or around 1 cm to 5 cm.

It is also preferable for the sticking part of the above protector to have an opening corresponding to the tube entry part and a cut that extends from the opening to an outer edge of the sticking part.

With the above construction, an opening is provided corresponding to the tube entry part, so that the sticking part can be stuck onto the skin so as to surround the tube entry part. In addition, a cut is provided from the opening to the outer edge of the sticking part, which facilitates the operation of sticking the sticking part in the periphery of the tube entry part.

It is also preferable for the sticking part of the above protector to be composed of at least two submembers in which concave parts are formed corresponding to the tube entry part.

With the above construction, by arranging the concave parts corresponding to the tube entry part, the sticking part can be stuck onto the skin so as to surround the tube entry part. Since the sticking part is split into two or more submembers, the operation of sticking the sticking part in the periphery of the tube entry part can be performed easily.

It is also preferable for the sticking part and the covering of the above protector to be composed of separate parts.

Since different properties are required for the sticking part and the covering, the constructions and/or materials also differ. By using separate parts as in the above construction, these parts can be manufactured easily, thereby facilitating the manufacturing process.

It is also preferable with the above protector for a coat of adhesive to be provided on one of the sticking part and the covering to fix the covering to the sticking part.

With the above construction, the covering can be attached to the sticking part by a simple operation. It is especially preferable for the coat of adhesive to be provided by sticking on double-sided adhesive tape.

It is also preferable with the above protector for a coat of adhesive to be provided on one of the covering and the cap to fix the cap to the covering.

With the above construction, the cap can be attached to the covering by a simple operation. It is especially preferable for the coat of adhesive to be provided by sticking on double-sided adhesive tape.

It is also preferable with the above protector for a coat of adhesive that fixes the tube fixing part to one of the sticking part and the covering to be provided on one of (i) the tube fixing part and (ii) one of the sticking part and the covering.

With the above construction, the tube fixing part can be attached to one of the sticking part and the covering by a simple operation. It is especially preferable for the coat of adhesive to be provided by sticking on double-sided adhesive tape.

It is also preferable with the above protector for the tube to be a tube that is used to connect a blood pump that is implanted in the living body and an external controller that controls the blood pump.

With the above construction, treatment following an operation that implants a blood pump can be performed safely and easily.

It is also preferable with the above protector for the tube to be a tube that circulates blood between the living body and a dialysis apparatus.

With the above construction, treatment performed using dialysis can be performed safely and easily.

It is also preferable with the above protector for the tube to be a tube that is implanted in the living body in order to perform continuous ambulatory peritoneal dialysis ("CAPD").

With the above construction, treatment performed using CAPD can be performed safely and easily.

A blood pump system according to the present invention includes: a blood pump; an external controller that controls the blood pump; a tube that is used to connect the blood pump and the external controller; and a protector as described above.

With the above blood pump system according to the present invention, the protector is used to make it extremely difficult for infections to occur at the tube entry part, so that the blood pump system is suited to treatment following an operation that implants a blood pump.

The cap according to the present invention is used with the protector described above. This means that the cap of the present invention is especially suited to the realization of a protector that makes it extremely difficult for infections to occur at a tube entry part.

The tube fixing part according to the present invention is used with the protector described above. This means that the tube fixing part of the present invention is especially suited to the realization of a protector that makes it extremely difficult for infections to occur at a tube entry part.

The covering according to the present invention is used with the protector described above. This means that the covering of the present invention is especially suited to the realization of a protector that makes it extremely difficult for infections to occur at a tube entry part.

The sticking part according to the present invention is used with the protector described above. This means that the sticking part of the present invention is especially suited to the realization of a protector that makes it extremely difficult for infections to occur at a tube entry part.

Another protector according to the present invention protects a part (hereinafter "equipment provided part") of a living body where medical equipment is disposed so as to pass through the skin from infection and includes: a sticking part that is stuck onto the skin of the living body in a periphery of the equipment provided part; and a covering that covers the equipment provided part and forms an internal space that surrounds the equipment provided part, wherein the covering is provided with an opening that can be freely opened and closed using a cap or the like.

With the above protector of the present invention, the equipment provided part is surrounded by the covering, so that it becomes difficult for external forces to act on the equipment provided part, thereby preventing the medical equipment from moving. This means that the external forces can be effectively prevented from detaching the medical equipment from the body tissue, which is effective in suppressing infections.

Also with the protector of the present invention, the internal space that surrounds the equipment provided part can be filled with medication, which is even more effective in preventing infections.

In addition, with the above protector of the present invention, an opening that can be freely opened and closed is provided for the internal space that surrounds the equipment provided part, so that via this opening, medication can be easily administered to the equipment provided part and the equipment provided part can be treated as necessary, which means that infections can be prevented even more effectively. Also, via this opening, air can pass through to the equipment provided part so as to dry the equipment provided part. This suppresses the propagation of germs and makes it possible to prevent infections even more effectively.

It is preferable for the above protector to further include a cap that closes the opening.

With the above construction, the cap can be normally closed. This prevents bacteria in the air from reaching the equipment provided part, so that infections can be prevented even more effectively.

It is also preferable for the cap of the above protector to be breathable and to function as a filter that prevents bacteria from entering.

With the above construction, moisture and bacteria can be prevented from entering by closing the cap. In addition, in this closed state air can pass through to the equipment provided part so as to dry the equipment provided part. This suppresses the propagation of germs and makes it possible to prevent infections even more effectively.

It is also preferable for the cap of the above protector to include an outer frame, which is made of a resinous material, and a film, which is disposed inside the outer frame and is breathable, the outer frame and the film being integrated. The outer frame and the film are integrated by adhesion, welding, insert molding or the like.

With the above construction, the outer frame is made of a resinous material, so that shocks experienced when the cap is opened and closed are dampened, which effectively prevents external forces from detaching the medical equipment from the body tissue. This also reduces the pain experienced by the patient when the cap is opened and closed. In addition, when the outer frame and breathable film are integrated, the construction of the cap is highly reliable, which means that infections can be prevented even more reliably.

With the above protector, it is also preferable for the film to be composed of a polyurethane film in which silk protein powder has been dispersed. This construction is suited to preventing moisture, bacteria, etc., from passing through the film while ensuring that the film is breathable.

BRIEF DESCRIPTION OF THE DRAWINGS

FIG. 13 is a drawing showing the assembly process performed when the protector according to the third embodiment of the present invention is attached to the tube entry part.

DETAILED DESCRIPTION OF THE EMBODIMENTS

The following describes several embodiments of the present invention in detail with reference to the attached drawings.

First Embodiment

Figure 1:
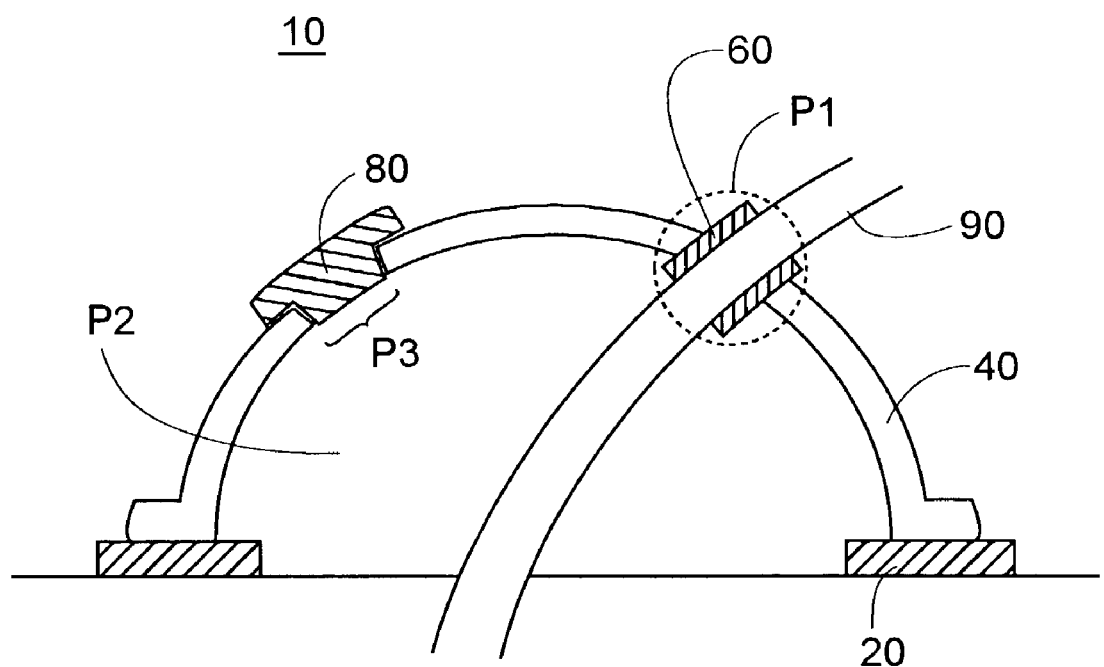
FIG. 1 is a cross-sectional drawing showing a protector according to a first embodiment of the present invention.

FIG. 1 is a cross-sectional drawing showing a protector according to a first embodiment of the present invention. As shown in FIG. 1, the protector 10 protects a tube entry part, where a tube 90 passes through the skin of a living body, from infections. The protector 10 includes a sticking part 20 that is stuck onto the skin of a living body in a periphery of the tube entry part and a covering 40 that covers the tube entry part, forms an internal space P2 that surrounds the tube entry part, and has a passage P1 through which the tube 90 passes. The covering 30 is also provided with an opening P3 that can be freely opened and closed using a cap 80.

In the protector 10, the covering 40 has a passage P1 through which the tube 90 passes, so that it is difficult for the tube 90 to move. This means that external forces can be effectively prevented from detaching the tube 90 from the body tissue. The protector 10 also provides an internal space P2 that surrounds the tube entry part and can be filled with medication. This is also effective in suppressing infections.

The protector 10 also includes an opening P3 to the internal space P2 surrounding the tube entry part. This opening P3 can be freely opened and closed so that via the opening P3, medication can be administered to the tube entry part and the tube entry part can be treated as necessary, which means that infections can be suppressed even more effectively. Since air can pass through the opening P3 to the tube entry part, the tube entry part can be dried. As a result, the propagation of germs can be suppressed and infections can be even more effectively prevented.

If the cap 80 is normally closed, bacteria in the air can be prevented from reaching the tube entry part, so that infections can be even more effectively suppressed.

As one example, the tube 90 may be a tube that is used to connect a blood pump that is implanted in the living body and an external controller that controls the blood pump. By using such a tube, treatment subsequent to an operation that implants a blood pump can be performed safely and smoothly.

Alternatively the tube 90 may be a tube that circulates blood between the living body and a dialysis apparatus. By using such a tube, treatment using dialysis can be performed safely and smoothly.

As yet another alternative, the tube 90 may be a tube that is implanted in the living body in order to perform CAPD. This makes it possible to perform treatment using CAPD safely and smoothly.

Modification

Figure 2:
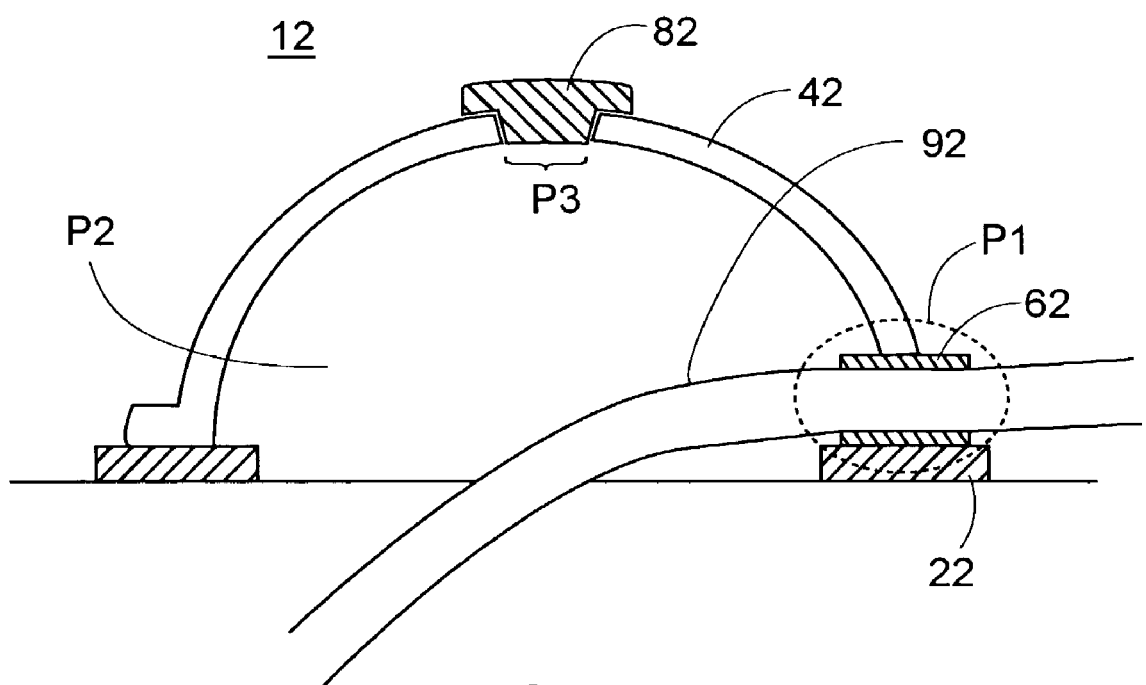
FIG. 2 is a cross-sectional drawing showing a protector according to a modification of the first embodiment of the present invention.

FIG. 2 is a cross-sectional drawing showing a protector 12 according to a modification of the first embodiment of the present invention. As shown in FIG. 2, the protector 12 protects a tube entry part where a tube 92 passes through the skin of a living body from infections. The protector 10 includes a sticking part 22 that is stuck onto the skin of a living body in a periphery of the tube entry part and a covering 42 that covers the tube entry part, forms an internal space P2 that surrounds the tube entry part, and has a passage through which the tube 90 passes. The covering 42 is also provided with an opening P3 that can be freely opened and closed using a cap 82. This means that the protector 12 has the same fundamental construction as the protector 10.

However, the protector 12 differs from the protector 10 in the position of the passage P1 through which the tube passes. In more detail, while the passage P1 of the protector 10 through which the tube passes is located in an approximate center of the covering, the passage P1 of the protector 12 is located at or near the outer edge of the covering 42.

As a result, with the protector 12, the tube 92 that sticks out of the living body can be disposed almost parallel to the surface of the skin of the living body, which makes it more difficult for external forces to affect the tube 92.

Second Embodiment

Figure 3:
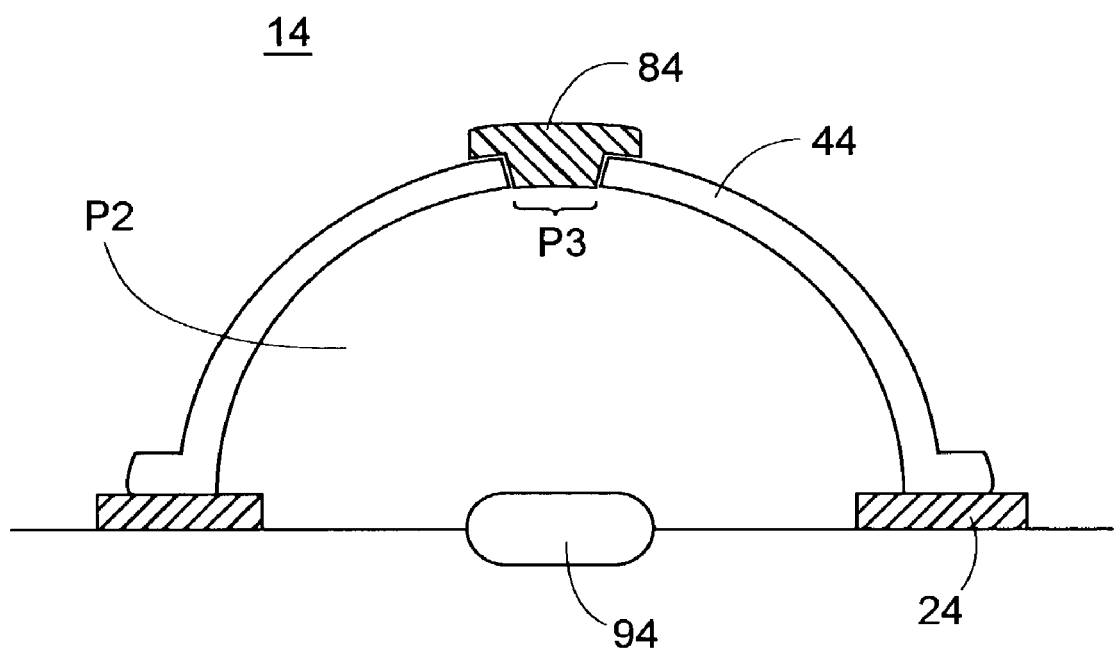
FIG. 3 is a cross-sectional drawing showing a protector according to a second embodiment of the present invention.

FIG. 3 is a cross-sectional drawing showing a protector according to a second embodiment of the present invention. As shown in FIG. 3, the protector 14 is a protector that protects a part (hereinafter "equipment provided part") of the skin of a living body where medical equipment 94 is disposed from infection. The protector 14 includes a sticking part 24 that is stuck onto the skin of a living body in a periphery of the equipment provided part and a covering 44 that covers the equipment provided part and forms an internal space P2 that surrounds the equipment provided part. The covering 44 is also provided with an opening P3 that can be freely opened and closed using a cap 84 or the like.

Since the covering 44 of the protector 14 surrounds the equipment provided part, external forces are prevented from acting on the equipment provided part, which makes it difficult for the medical equipment 94 to move. This means that the external forces are effectively prevented from detaching the medical equipment 94 from the body tissue.

Using the protector 14, it is also possible to fill the internal space P2 surrounding the equipment provided part with medication, so that infections can be effectively prevented.

The protector 14 is provided with an opening P3 to the internal space P2 surrounding the equipment provided part, with it being possible to freely open and close this opening P3. Via this opening P3, medication can be administered to the equipment provided part and the equipment provided part can be treated as necessary, which makes it possible to prevent infections even more effectively. Since air can pass through the opening P3 to the equipment provided part, the equipment provided part can be dried, which suppresses the propagation of germs and makes it possible to prevent infections even more effectively.

If the cap 84 is normally closed, bacteria in the air can be prevented from reaching the equipment provided part, so that infections can be prevented even more effectively.

The cap 84 can be made of a breathable material. This means that even when the cap 84 is closed, air can be allowed to pass through to the equipment provided part, so that infections can be prevented even more effectively.

Third Embodiment

The following describes, with reference to FIGS. 4 to 14, a protector according to a third embodiment of the present invention.

Figure 4:
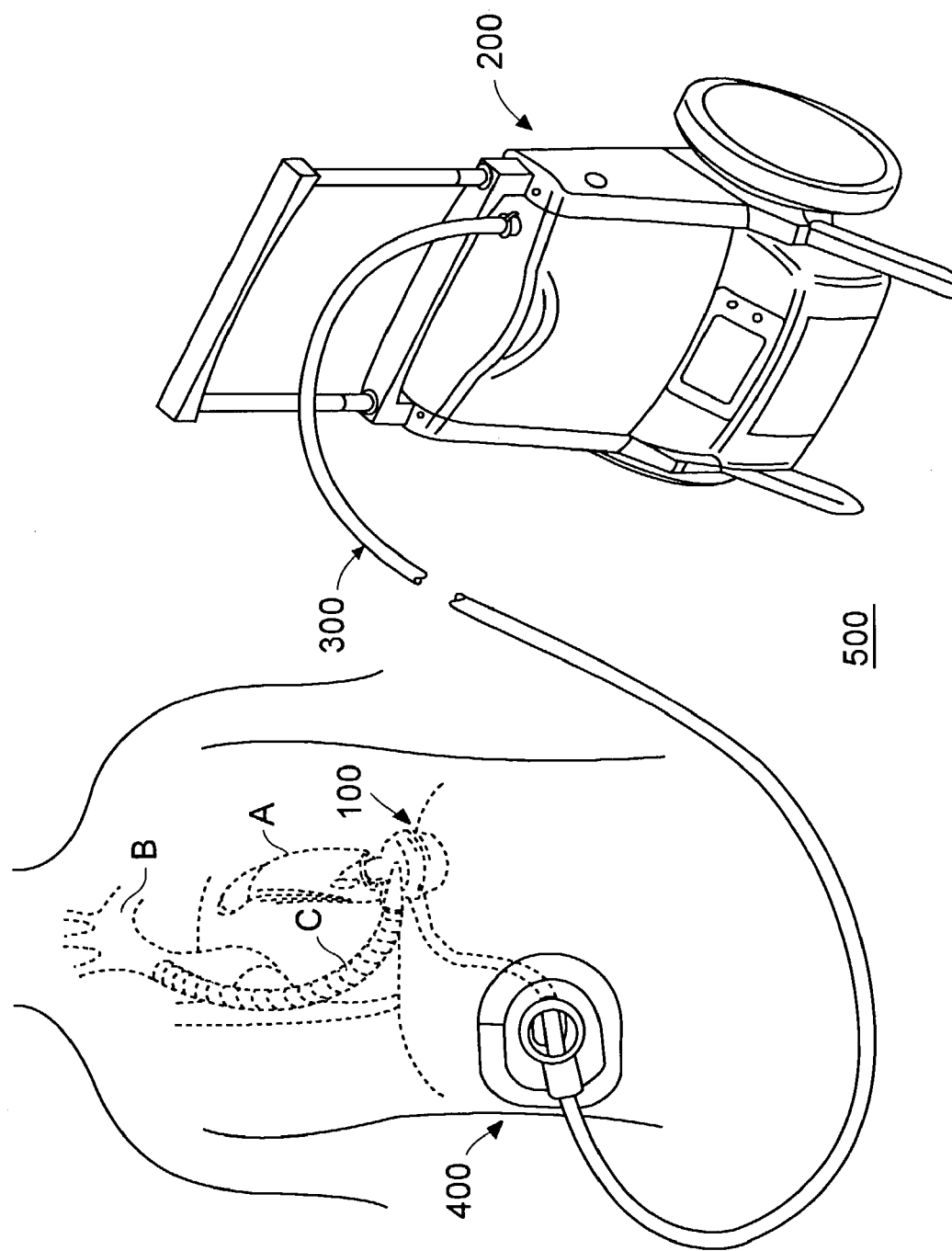
FIG. 4 is a drawing showing a blood pump system according to a third embodiment of the present invention.

FIG. 4 is a drawing showing a blood pump system 500 that uses a protector 400 according to the third embodiment of the present invention. As shown in FIG. 4, the blood pump system 500 of the third embodiment includes a blood pump 100, an external controller 200 that controls the blood pump 100, a tube 300 that is used to connect the blood pump 100 and the external controller 200, and the protector 400 that protects the tube entry part from infections.

Figure 5:
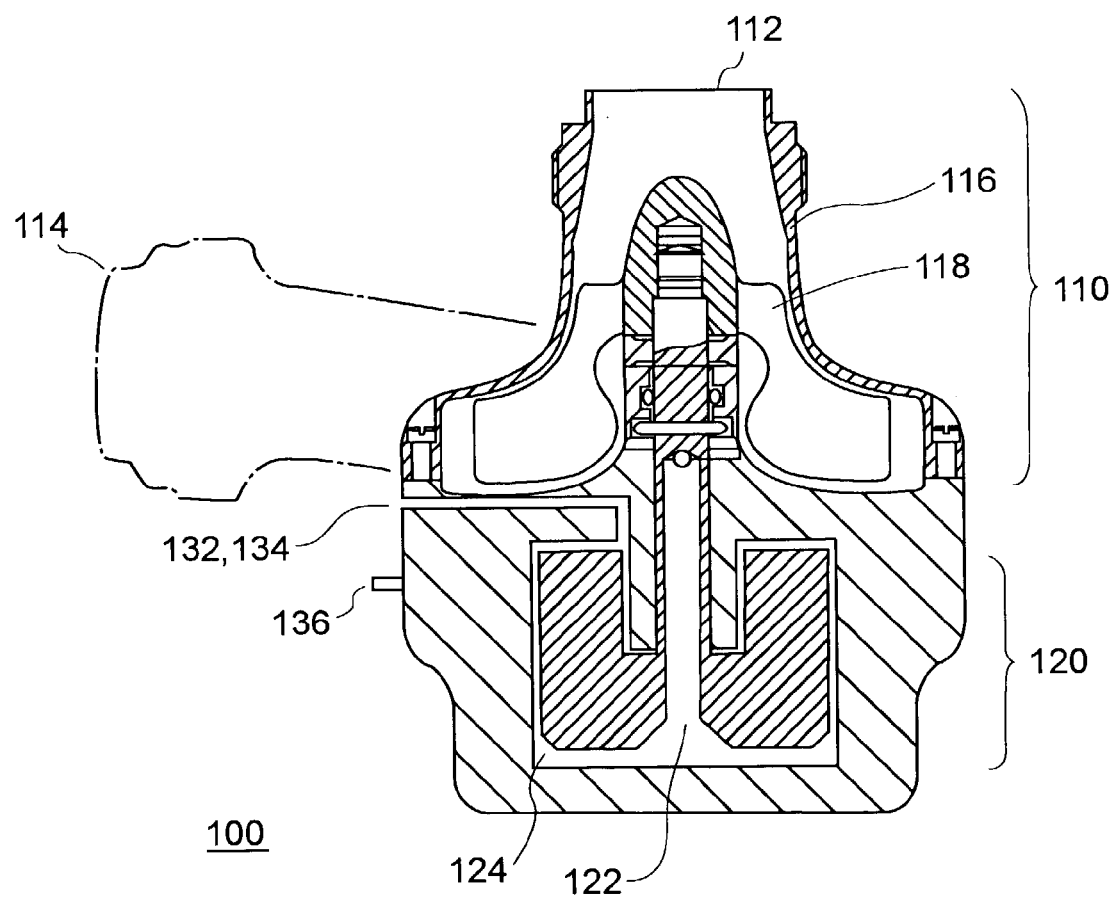
FIG. 5 is a drawing showing a blood pump according to the third embodiment of the present invention.

FIG. 5 is a drawing showing the blood pump 100 that is used in the blood pump system 500 shown in FIG. 4. As shown in FIG. 5, the blood pump 100 includes a pump base section 120, which has a cylindrical motor, and a pump section 110, which is connected to the pump base section 120. The pump section 110 includes pump vanes 118 that are driven via a rotational shaft of the motor and a casing 116 that is connected to the pump base section 120 so as to cover the pump vanes 118. Blood in the left ventricle A flows into the casing 116 from an intake 112 provided at the end of the casing 116, the blood is energized by the pump vanes 118 in the casing 116, and the blood is then discharged into the aorta B via an outtake 114 provided in the side of the casing 116 and an artificial blood vessel C.

An end-contact-type blood seal (hereinafter, "mechanical seal") is provided between the pump base section 120 and the pump vanes 118, so as to stop blood constituents from seeping into and coagulating in the bearings of the rotational shaft of the motor. The pump base section 120 is also provided with an intake 132 and an outtake 134 for a circulating fluid (though not clear in FIG. 5, the inlet 132 and the outlet 132 are provided separately perpendicular to the plane of the drawing). This intake 132 and the outtake 134 for the circulating fluid are connected to the external controller 200 via inner tubes 302 (see FIG. 6) that are enclosed in the tube 300. The external controller 200 includes a circulating liquid pump that circulates the circulating liquid to the periphery of the mechanical seal. As a result, lubrication, cooling, and dispersion occur at the sliding surfaces of the mechanical seal. In addition, a filter provided in the external controller 200 removes fine particles of blood constituents that enter the circulating fluid so as to constantly keep the sliding surfaces of the mechanical seal and the bearings clean.

A centrifugal pump, an axial-flow pump, a mixed-flow pump, or the like can be favorably used as the blood pump 100. Also, the blood seal is not limited to a mechanical seal, so that an oil seal or other type of contact seal may be used.

The external controller 200 has a system driving section including the circulating liquid pump that supplies the circulating liquid to the periphery of the mechanical seal of the blood pump 100, a pump control unit that electrically controls the driving of the blood pump 100 via a cable 304 that is enclosed in the tube 300, a display unit that displays data and the operating states of the various components, a communication unit that exchanges information with external devices, a power supplying unit that supplies these components with electrical power, and a control unit for controlling these components. This system driving section is enclosed in a compact case.

Also, while the external controller 200 in the present embodiment is in the form of a cart that is pushed by hand, the external controller 200 may be alternatively produced in the form of a wheelchair or a bag, so that a form that is suited to the condition and living arrangements of the patient may be used. An electric mobile controller may also be used by attaching a motor to the wheels.

Figure 6:
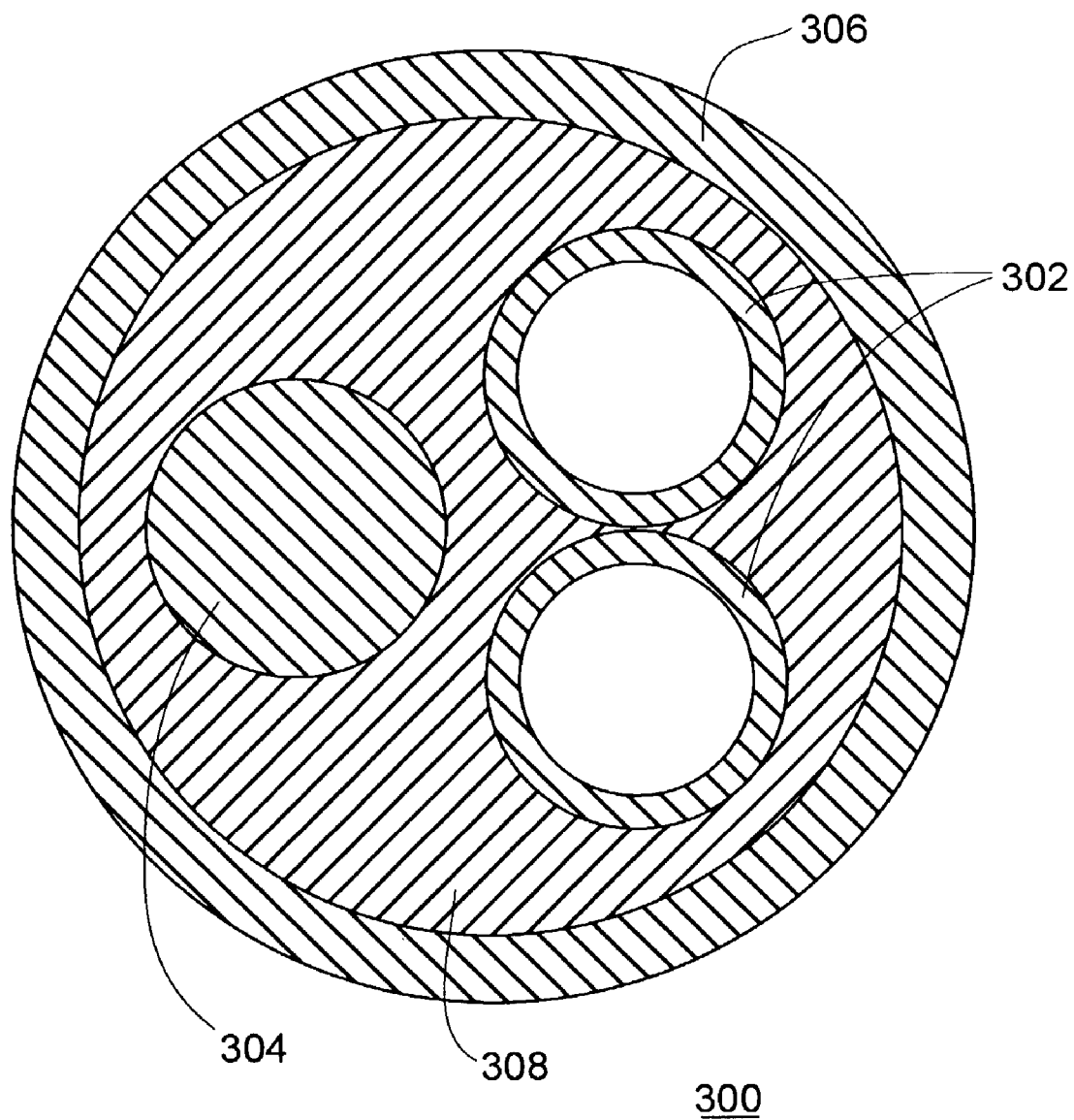
FIG. 6 is a drawing showing a tube according to the third embodiment of the present invention.

FIG. 6 is a drawing showing the tube 300 used in the blood pump system 500 shown in FIG. 4. As shown in FIG. 6, the tube 300 of the third embodiment is a tube that connects the blood pump 100 and the external controller 200 that controls the blood pump 100. The tube 300 includes inner tubes 302 for circulating liquid between the blood pump 100 and the external controller 200, a cable 304 that includes electric wires that are connected to the blood pump 100, and an outer tube 306 in which the inner tubes 302 and the cable 304 are enclosed.

As a result, with the tube 300 according to the third embodiment, the inner tubes 302, the cable 304, etc., are unaffected by stretching and bending caused by movements of the living body or the application of external forces, so that the inner tubes 302 are protected against deformation and the cable 304 is protected against breakages. With the tube 300 according to the third embodiment, only one entry point (the tube entry part) into the living body is required, which can minimize the influence on the living body.

The tube 300 according to this third embodiment includes two inner tubes 302, with these two inner tubes 302 being used to circulate pure water between the blood pump 100 and the external controller 200. The pure water acts as a coolant for the motor unit in the blood pump 100, as a lubricant for the sliding parts of the blood seal, and as a sealant that provides a seal between the motor unit and the blood pump unit. Also, by having pure water circulated between the blood pump 100 and the external controller 200, the motor can be effectively prevented from coming to a stop since any blood that enters the motor is diluted by the pure water, which stops the blood from coagulating. The pure water is also filtered, so that any blood constituents that enter the pure water can be removed, thereby making the system even more effective at preventing blood from stopping the rotation of the motor. Also, by having the pure water circulated, heat inside the blood pump can be effectively dissipated.

Figure 7:
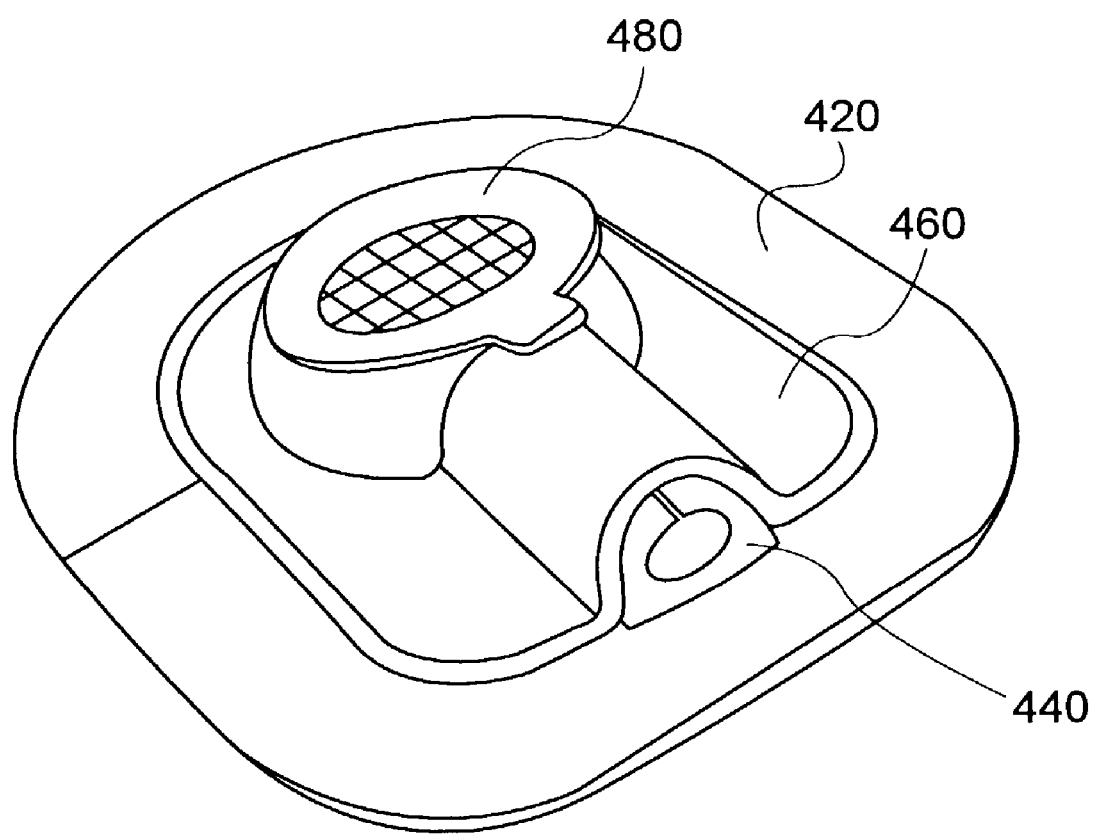
FIG. 7 is a perspective view of a protector according to the third embodiment of the present invention.
Figure 8:
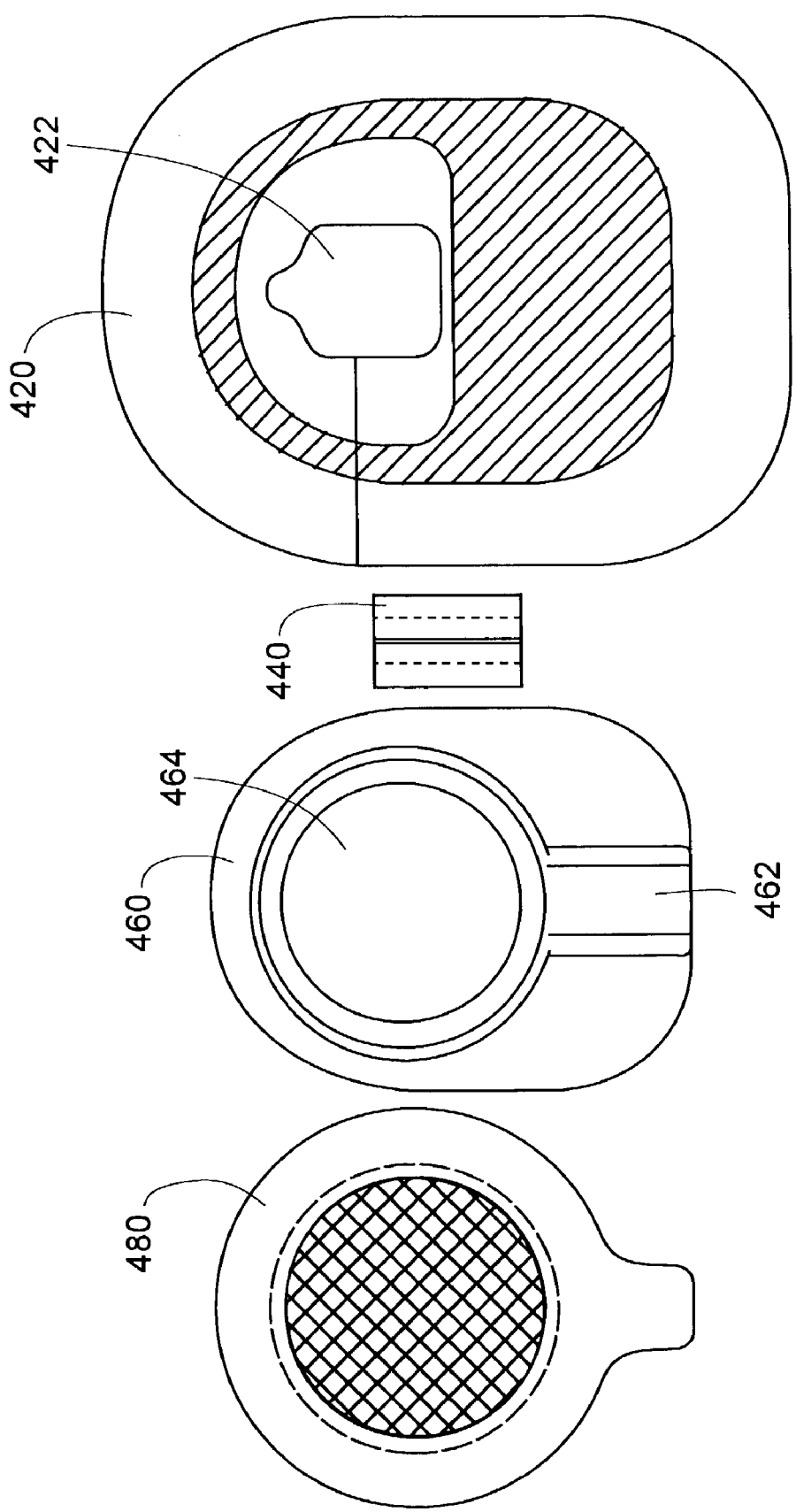
FIG. 8 is a drawing showing each of the components that compose the protector according to the third embodiment of the present invention.
Figure 9:
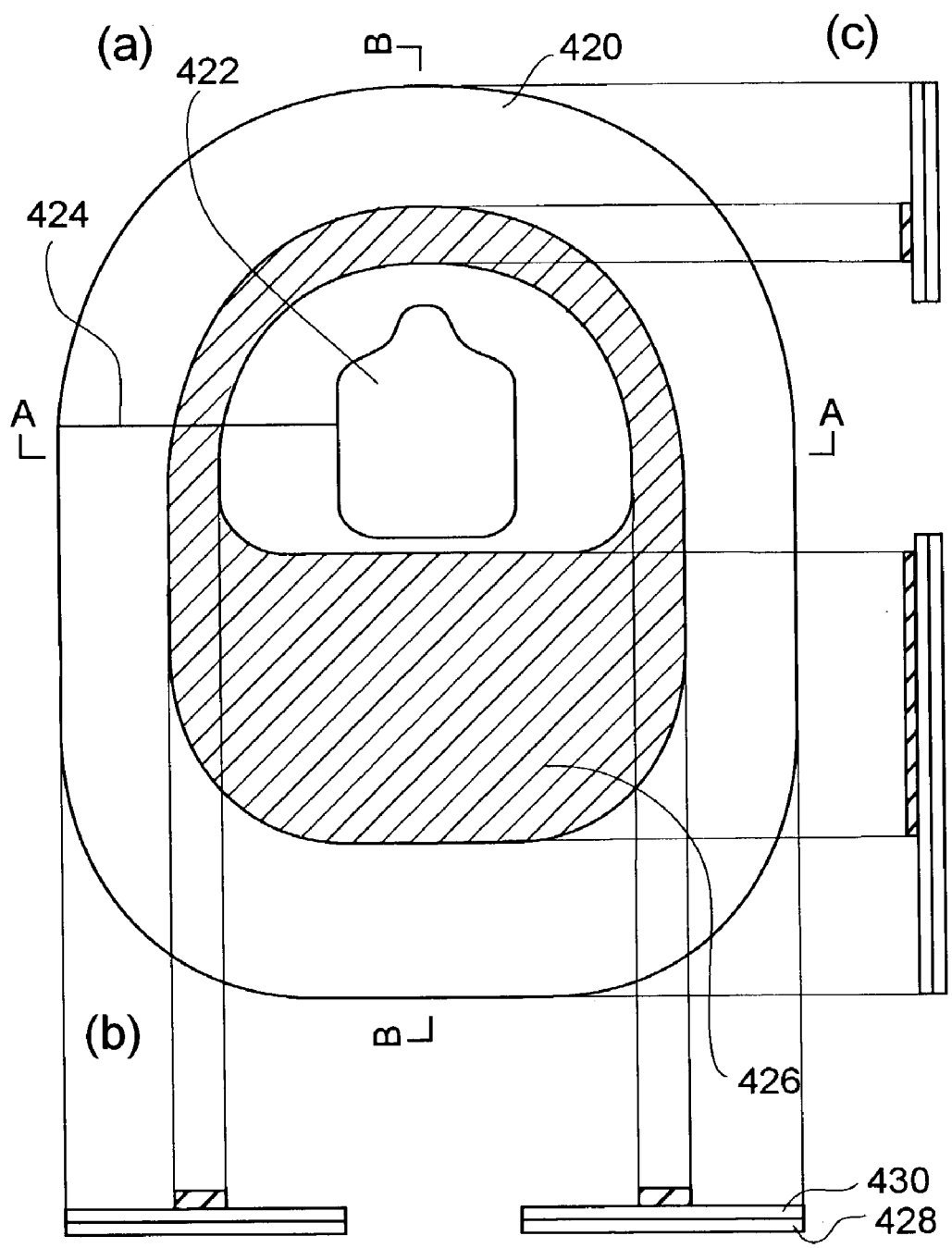
FIG. 9 is a three-view drawing of a sticking part that forms part of the protector according to the third embodiment of the present invention.
Figure 10:
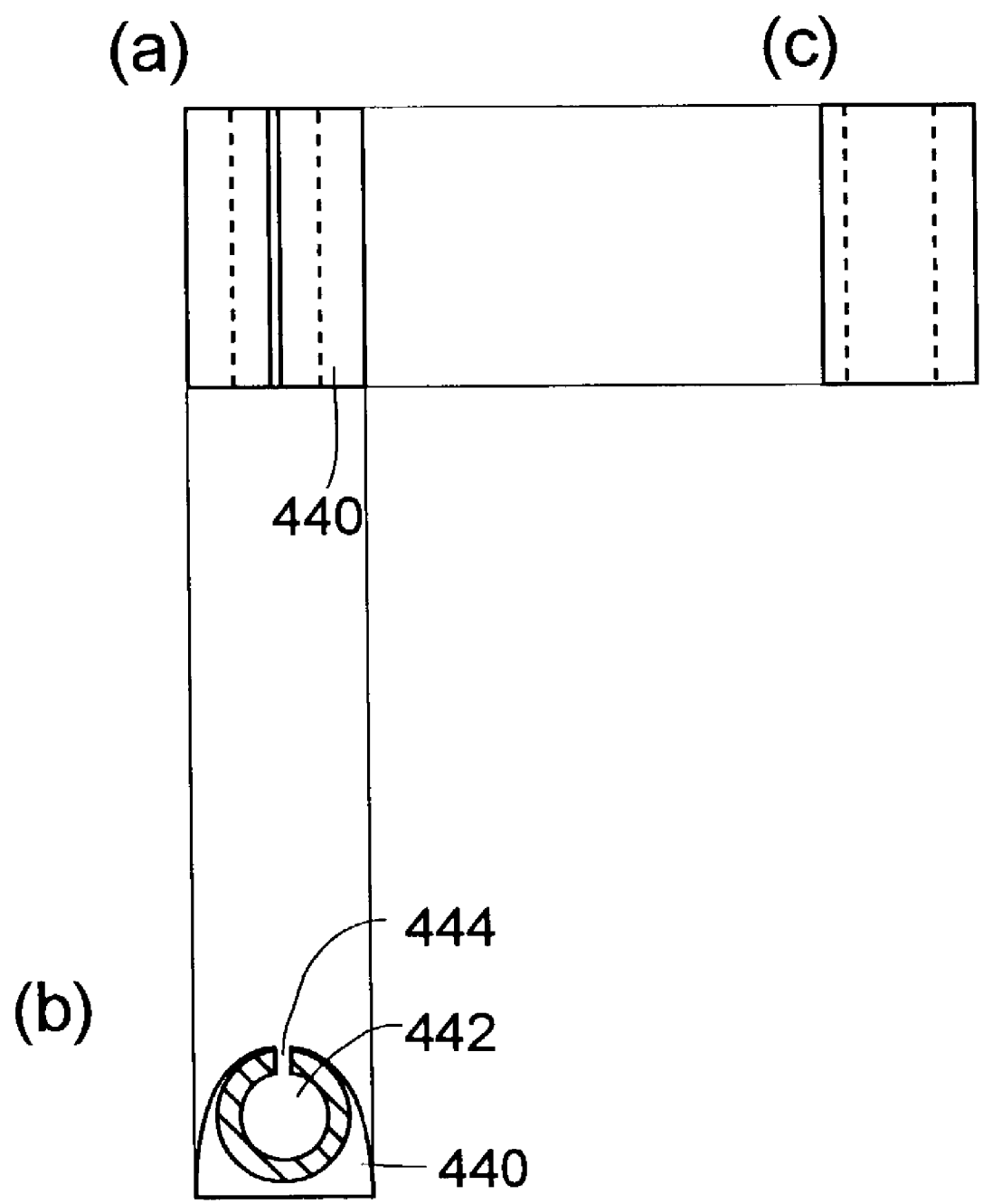
FIG. 10 is a three-view drawing of a tube fixing part that forms part of the protector according to the third embodiment of the present invention.
Figure 11:
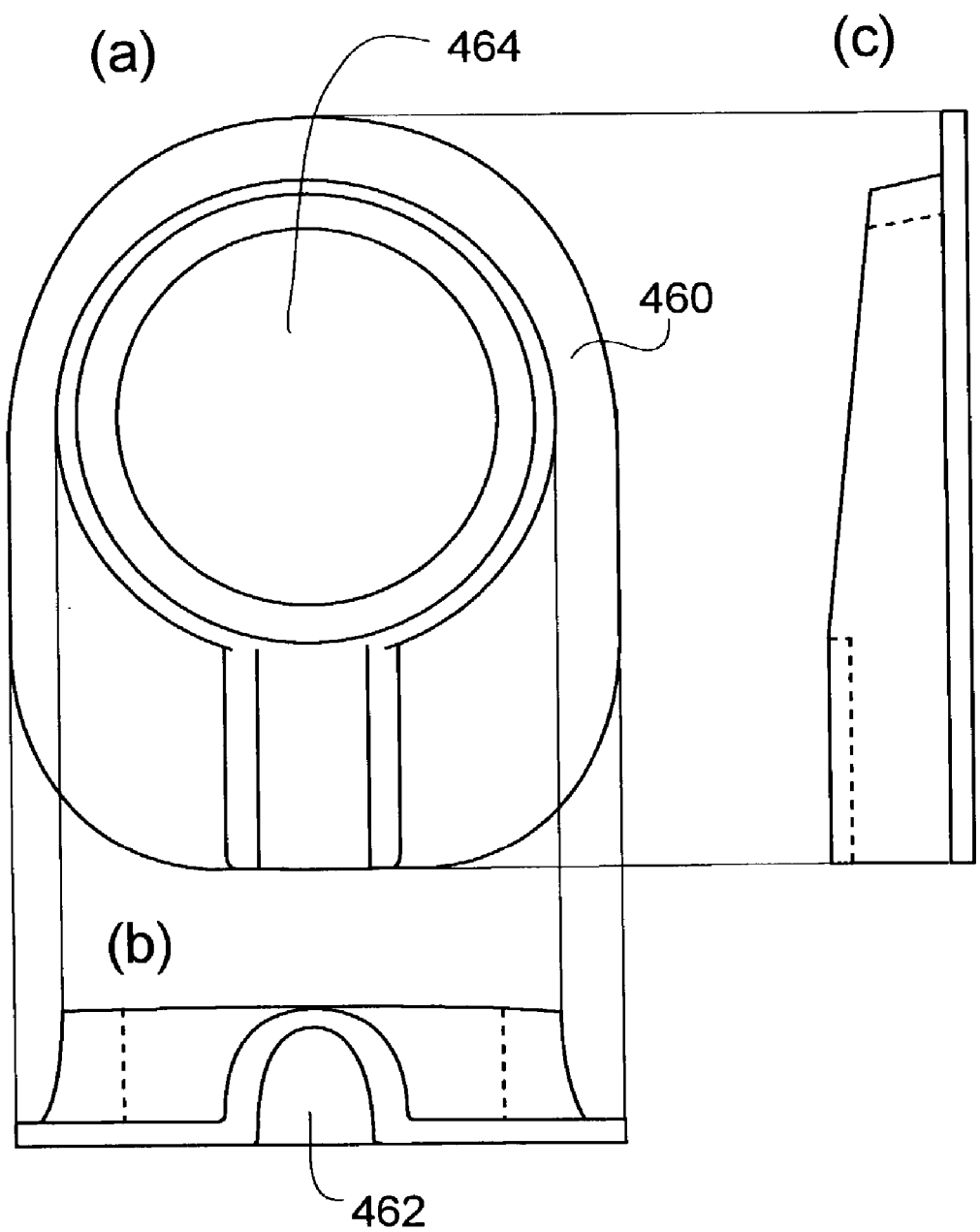
FIG. 11 is a three-view drawing of a covering that forms part of the protector according to the third embodiment of the present invention.
Figure 12:
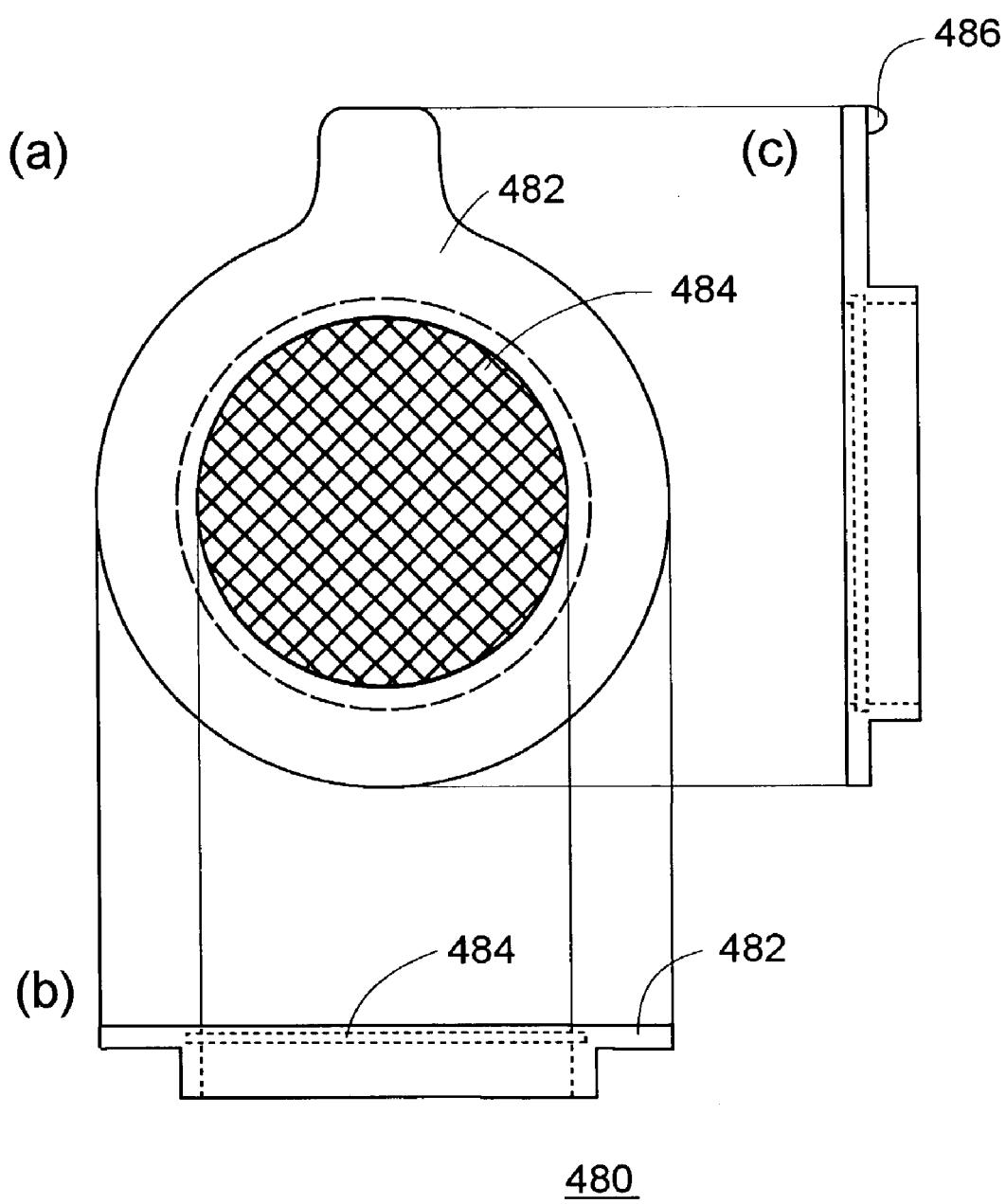
FIG. 12 is a three-view drawing of a cap that forms part of the protector according to the third embodiment of the present invention.
Figure 14A:
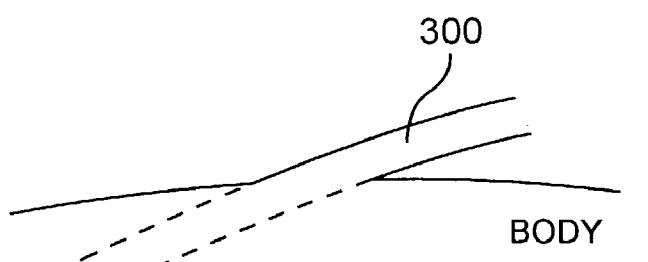
FIG. 14 is a drawing showing the assembly process performed when the protector according to the third embodiment of the present invention is attached to the tube entry part.
Figure 14B:
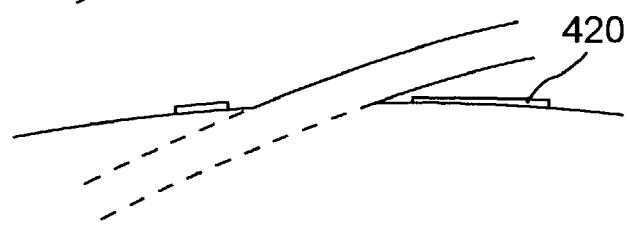
Figure 14C:
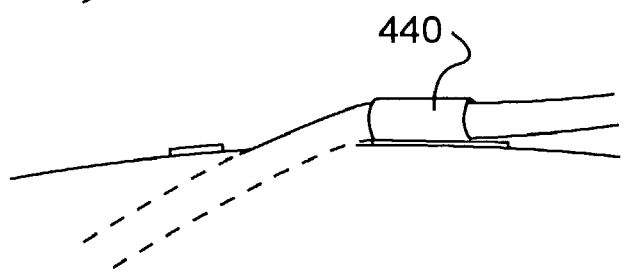
Figure 14D:
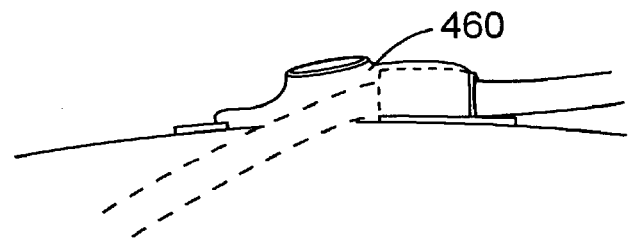
Figure 14E:
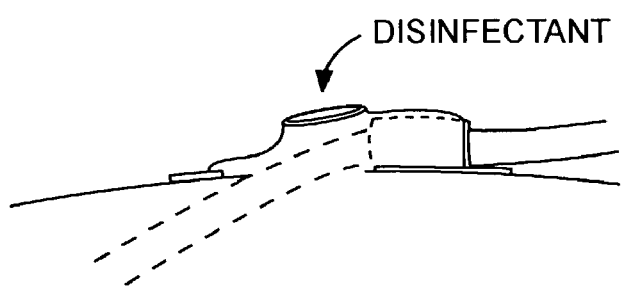
Figure 14F:
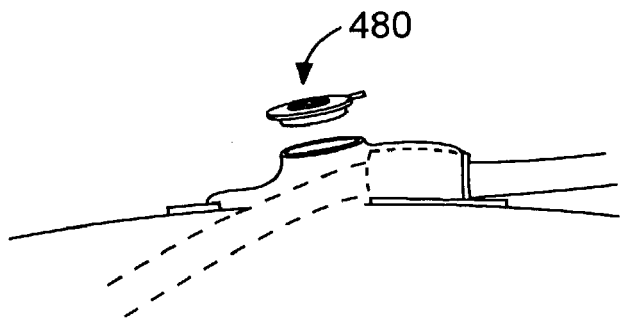

FIG. 7 is a perspective view of the protector 400 according to the third embodiment of the present invention. FIG. 8 is a drawing showing the components that compose the protector 400 according to the third embodiment of the present invention. FIG. 9 is a three-view drawing of a sticking part 420 that forms part of the protector 400 according to the third embodiment of the present invention. FIG. 10 is a three-view drawing of a tube fixing part 440 that forms part of the protector according to the third embodiment of the present invention. FIG. 11 is a three-view drawing of a covering 460 that forms part of the protector 400 according to the third embodiment of the present invention. FIG. 12 is a three-view drawing of a cap 480 that forms part of the protector 400 according to the third embodiment of the present invention.

As shown in FIGS. 7 and 8, the protector 400 according to the third embodiment protects the tube entry part where the tube 300 passes through the skin of a living body from infection, and includes a sticking part 420 that is stuck onto the skin of the living body in a periphery of the tube entry part and a covering 460 that covers the tube entry part, forms an internal space that surrounds the tube entry part, and has a passage 462 through which the tube 300 passes. In addition, the covering is provided with an opening 464 that can be freely opened and closed with a cap or the like. The protector 400 also includes a tube fixing part 440 for fixing the tube 300 to the protector 400. The protector 400 also includes a cap 480 for closing the opening 464.

FIG. 9 is a three-view drawing of the sticking part 420 that forms part of the protector 400 according to the third embodiment of the present invention. As shown in FIG. 9, the sticking part 420 includes an opening 422 corresponding to the tube entry part and a cut 424 that extends from the opening 422 to the outer edge of the sticking part 420. This means that the sticking part 420 can be stuck onto the skin so as to surround the tube entry part. The presence of the cut 424 makes it easier to stick the sticking part 420 in a periphery of the tube entry part. To make the protector easy to use, the size of the opening 422 in the sticking part 420 is set at 2 cm on the minor axis and 4 cm on the major axis.

In addition, double-sided adhesive tape 426 is stuck onto the sticking part 420 in order to fix the covering 460 and/or the tube fixing part 440 to the sticking part 420. This facilitates the operation that fixes the covering 460 onto the sticking part 420. Double-sided adhesive tape may be stuck onto the covering 460 and/or the tube fixing part 440.

The sticking part 420 has a multilayer construction including a foam layer 430 and an adhesive layer 428. To make the entire sticking part flexible and to make it easy to attach the sticking part 420 to the skin by adhesion, the sticking part 420 is capable of bending in accordance with the form of the skin at the part where the sticking part 420 is to be attached. This makes it easy to attach the protector 400 to the skin and pressure sores and the like can be avoided. The sticking part 420 is also light, which reduces the burden on patients.

The foam layer 430 is formed of polyisobutylene foam. Polyisobutylene foam is compatible with medications such as ointments, so that many different medications can be selected.

The adhesive layer 428 is composed of a skin protective agent. This reduces the burden on the skin, so that the protector 400 can be used for a long period. A mixture that is made mostly from karaya gum and citrus pectin is used as the skin protective agent. Before the sticking part 420 is used, the adhesive surface is protected by providing backing paper on the surface of the adhesive layer 428.

The thickness of the sticking part 420 can be set appropriately for factors such as the position of the tube entry part and the thickness of the tube, though in this third embodiment, the sticking part 420 is set at 3.3 mm thick. The foam layer is 1.4 mm thick and the adhesive layer is 1.9 mm thick.

With this embodiment, sticking part 420 may also have a singlelayer construction including an adhesive layer.

FIG. 10 is a three-view drawing of a tube fixing part 440 that forms part of the protector 400 according to the third embodiment of the present invention. As shown in FIGS. 7, 8, and 10, the protector 400 according to the third embodiment includes the tube fixing part 440. This means that the tube 300 is prevented from moving even more effectively, so that external forces can be even more effectively prevented from detaching the tube 300 from the body tissue.

The tube fixing part 440 is stuck onto the sticking part 420 using double-sided adhesive tape and is constructed so that its outer part is enclosed within a concave part 462 of the covering 460. The inner surface of the tube fixing part 440 corresponds to the outer surface of the tube 300 and the tube fixing part 440 has a hole 442 with a cut 444 that extends in the axial direction. This means that the tube 300 is fixed to the protector 400 via the tube fixing part 440, so that the tube 300 is reliably prevented from moving. In the same way, since the inner surface of the tube fixing part 440 corresponds to the outer surface of the tube 300, the tube 300 is reliably prevented from moving and bacteria can be totally prevented from entering the internal space that surrounds the tube entry part. Also, since the cut 444 is provided for the hole 442 in the axial direction, it is easy to pass the tube 300 through the hole 442 and to remove the tube 300 from the hole 442.

A silicone tube with a Shore hardness of 40 A is used as the tube fixing part 440. This means that the cut 444 can be easily opened with the fingers, which makes it easy to fix (remove) the tube 300 to (from) the protector 400.

With this embodiment, the tube fixing part 440 can be integrated with the sticking part 420 or the covering 460 from the beginning.

FIG. 11 is a three-view drawing of a covering 460 that forms part of the protector 400 according to the third embodiment of the present invention. As shown in FIGS. 7, 8, and 11, the protector 400 according to the third embodiment has a covering 460. This makes it even more difficult for the tube 300 to move and means that external forces can be effectively prevented from detaching the tube 300 from the body tissue. Also, with the protector 400 according to the third embodiment, the internal space that surrounds the tube entry part can be filled with medication. In this way, infections can be effectively prevented.

Also with the protector 400 according to the third embodiment, an opening 464 that can be freely opened and closed is provided in the covering 460. This means that via the opening 464, medication can be administered to the tube entry part and the tube entry part can be treated as necessary, which means that infections can be prevented even more effectively. Since air can pass through the opening 464 to the tube entry part, the tube entry part can be dried. As a result, the propagation of germs can be suppressed and infections can be prevented even more effectively.

Silicone rubber with a Shore hardness of 40 A is used as the covering 460. This protects the sticking part 420 from the application of stress, which makes it difficult for the covering 460 to come off the sticking part 420. Also, the entire sticking part 420 can be made flexible so as to bend according to the shape of the body, which means that pressure sores and the like can be avoided. The covering 460 also has a certain degree of rigidity, so that the form of the internal space can be maintained. Double-sided adhesive tape is also stuck to the covering 460 in order to attach the cap 480. This makes it simple to fix the cap 480 to the covering 460. Double-sided adhesive tape may be attached to the cap 480.

FIG. 12 is a three-view drawing of a cap 480 that forms part of the protector 400 according to the third embodiment of the present invention. As shown in FIG. 12, the cap 480 of the protector 400 according to the third embodiment has an outer frame 482 that is formed of a resinous material and a breathable film 484 that is disposed on the inside of this outer frame 482 and integrated with the outer frame 482.

Since the outer frame 482 is formed of a resinous material, the shock that occurs when the cap 480 is opened and closed is dampened, so that external forces can be effectively prevented from detaching the tube 300 from the body tissue. Additionally, the pain experienced by the patient when the cap 480 is opened and closed can be reduced. The outer frame 482 is integrated with a breathable film 484, giving the cap 480 a reliable construction which is effective in preventing infections. The outer frame 482 is formed of a polyester elastomer with a Shore hardness of 50 A, and may be integrally formed with the film inside it by adhesion, welding, insert molding or the like.

Since a breathable film is used, even when the cap 480 is closed, air is allowed to pass through to the tube entry part, so that infections can be even more effectively prevented.

The film 484 is composed of a polyurethane film in which silk protein powder has been dispersed. This means that while the film is breathable, bacteria do not pass through the film, so that infections can be prevented even more effectively.

If the cap 464 of the protector 400 according to the third embodiment is normally closed, bacteria in the air can be prevented from reaching the tube entry part, so that infections can be even more effectively prevented.

FIGS. 13 and 14 show the assembly process performed when the protector according to the third embodiment of the present invention is attached to the tube entry part. As shown in FIGS. 13 and 14, the protector 400 according to the third embodiment is stuck onto the right side of the abdomen of a human body (see FIG. 4).

(1) First, the sticking part 420 is oriented with the adhesive layer facing downwards and is stuck to the periphery of the tube entry part so that the opening 422 is located over the tube entry part. At this point, the cut 424 of the sticking part 420 is opened so that no external force acts on the tube.

(2) Next, the tube fixing part 440 is stuck onto a predetermined position on the sticking part 420, with the backing paper first having been peeled off the double-sided adhesive tape 426. At this point, the cut in the tube fixing part 440 is opened so that the tube is inserted into the tube fixing part 440 without an external force being applied to the tube.

(3) Next, the covering 460 is stuck onto a predetermined position on the sticking part 420. During this operation, the tube fixing part 440 is fitted under the covering 460.

(4) Next, the tube entry part is disinfected via the opening 464 in the covering 460. After this, in order to provide long-term protection against infections, a predetermined amount of a predetermined ointment medication is added to the internal space formed by the covering 460 around the tube entry part.

(5) Finally, double-sided adhesive tape is used to stick the cap 480 over the part of the covering 460 including the opening 464.

As described above, the protector 400 according to the third embodiment can be assembled by sticking on the four component parts with the correct order, so that the protector 400 can be attached to the body without applying an excessive force, which is to say, without causing excessive discomfort to the body.

Modification

Figure 15:
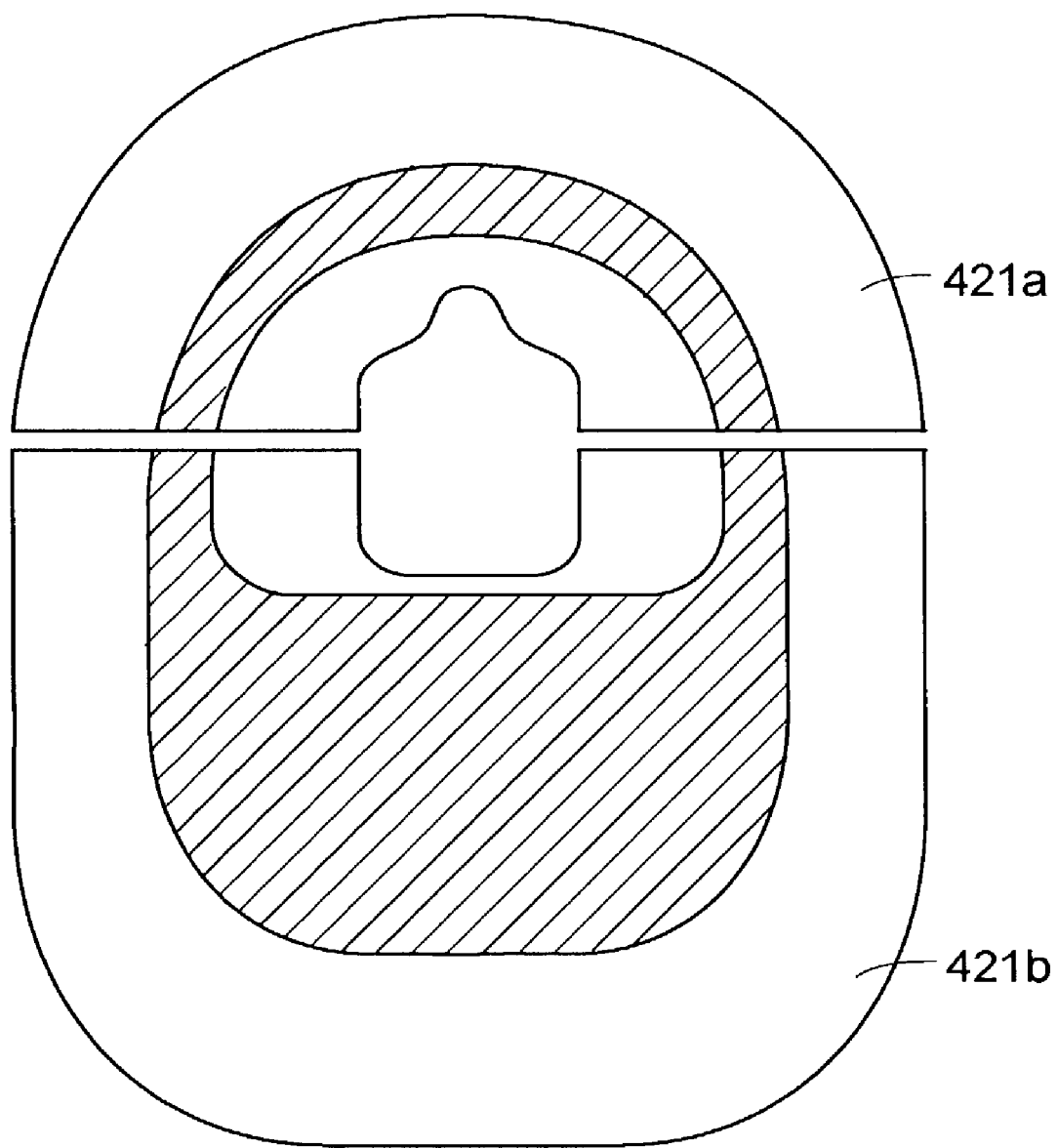
FIG. 15 is a top plan view of the sticking part that forms part of the protector according to a modification of the third embodiment of the present invention.
Figure 16:
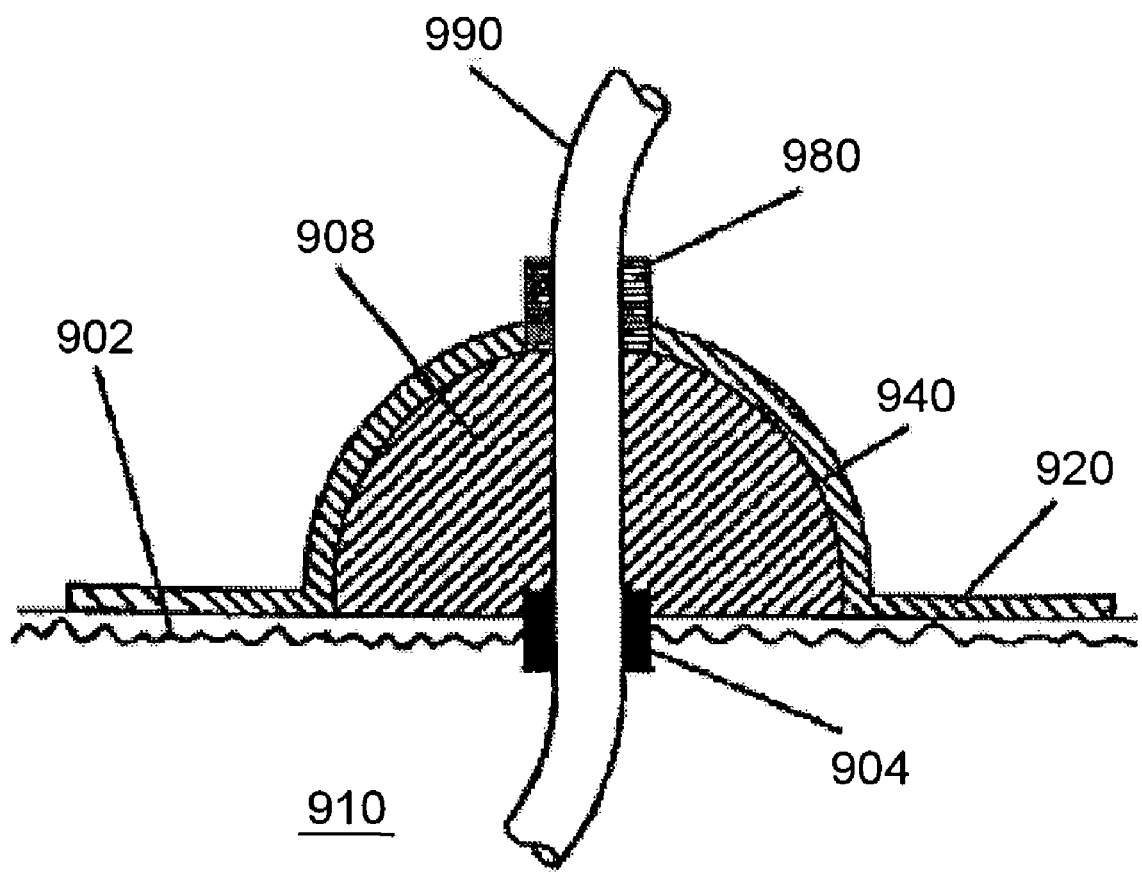
FIG. 16 is a cross-sectional drawing showing a conventional protector.

FIG. 15 is a top plan view of the sticking part that forms part of the protector according to a modification of the third embodiment of the present invention. As shown in FIG. 15, the sticking part 421 is composed of two submembers 421*a* and 421*b* in which concave parts are formed corresponding to the tube entry part. This means that by disposing these two submembers with the concave parts facing the tube entry part, the sticking part 421 can be stuck onto the skin so as to surround the tube entry part. Also, when the sticking part is split into two (or more) submembers, it is easy to stick the sticking part around the tube entry part.

What is claimed is:

1. A protector that protects a part (hereinafter "tube entry part"), where a tube or a cable (hereinafter "tube") is adapted to pass through the skin of a living body, from infection, the protector comprising:

a sticking part that is adapted to be stuck onto the skin of the living body in a periphery of the tube entry part so that the periphery of the tube entry part is surrounded by the sticking part;

a covering that covers the tube entry part, forms an internal space that surrounds the tube entry part and can be filled with medication, and has a passage through which the tube passes; and a cap, wherein the covering is provided with an opening that can be freely opened and closed by the cap; wherein said cap is breathable and functions as a filter that prevents bacteria from entering, said cap further comprising a rigid outer frame, which is made of a resinous material, and a film, which is disposed inside the outer frame and is breathable, the outer frame and the film being integrated.

2. A protector according to claim 1, wherein the film is composed of a polyurethane film in which silk protein powder has been dispersed.

3. A protector according to claim 1, further comprising a tube fixing part that fixes the tube to the protector.

4. A protector according to claim 3, wherein the tube fixing part is capable of being fixed to one of the sticking part and the covering and has a hole whose inner surface corresponds to an outer surface of the tube, a cut being provided in the tube fixing part in the axial direction.

5. A protector according to claim 3, wherein a coat of adhesive that fixes the tube fixing part to one of the sticking part and the covering is provided on one of (i) the tube fixing part and (ii) one of the sticking part and the covering.

6. A protector according to claim 1, wherein the sticking part has a multilayer construction including a foam layer and an adhesive layer or single layer construction including an adhesive layer.

7. A protector according to claim 3, wherein the foam layer is formed of polyisobutylene foam.

8. A protector according to claim 3, wherein the adhesive layer is formed of a skin protective agent.

9. A protector according to claim 1, wherein the sticking part has an opening corresponding to the tube entry part and a cut that extends from the opening to an outer edge of the sticking part.

10. A protector according to claim 1, wherein the sticking part is composed of at least two submembers in which concave parts are formed corresponding to the tube entry part.

11. A protector according to claim 1, wherein the sticking part and the covering are composed of separate parts.

12. A protector according to claim 11, wherein a coat of adhesive is provided on one of the sticking part and the covering to fix the covering to the sticking part.

13. A protector according to claim 1, wherein a coat of adhesive is provided on one of the covering and the cap to fix the cap to the covering.

* * * * *

UNITED STATES PATENT AND TRADEMARK OFFICE
CERTIFICATE OF CORRECTION

| | |
|---|---|
| PATENT NO. | : 7,344,512 B2 |
| APPLICATION NO. | : 10/387053 |
| DATED | : March 18, 2008 |
| INVENTOR(S) | : Yamazaki et al. |

Page 1 of 1

It is certified that error appears in the above-identified patent and that said Letters Patent is hereby corrected as shown below:

Column 16

In Claim 7 lines 39-40, change "A protector according to claim 3" to --A protector according to claim 6--.

In Claim 8 lines 41-42, change "A protector according to claim 3" to --A protector according to claim 6--.

Signed and Sealed this

Eleventh Day of November, 2008

JON W. DUDAS
*Director of the United States Patent and Trademark Office*